United States Patent [19]

Frankfurt et al.

[11] Patent Number: 5,370,866
[45] Date of Patent: Dec. 6, 1994

[54] COLORLESS OR COLORED NAIL POLISH CONTAINING ARAMIDE FIBERS

[75] Inventors: Christopher C. Frankfurt, Old Bridge; Alan M. Farer, Morganville; Adrian J. Penicnak, Mountain Lakes, all of N.J.

[73] Assignee: L'Oreal, Paris, France

[21] Appl. No.: 956,895

[22] PCT Filed: Apr. 30, 1992

[86] PCT No.: PCT/FR92/00401

§ 371 Date: Apr. 5, 1993

§ 102(e) Date: Apr. 5, 1993

[87] PCT Pub. No.: WO92/19282

PCT Pub. Date: Nov. 12, 1992

[30] Foreign Application Priority Data

May 2, 1991 [FR] France ................. 91 05395

[51] Int. Cl.$^5$ ............................................. A61K 7/04
[52] U.S. Cl. ........................................ 424/61; 523/105
[58] Field of Search ........................... 424/61; 523/105

[56] References Cited

U.S. PATENT DOCUMENTS

| 4,822,423 | 4/1989 | Soyama et al. | 106/5 |
| 4,873,077 | 10/1989 | Thompson et al. | 424/61 |

FOREIGN PATENT DOCUMENTS

| 1529329 | 6/1968 | France . |
| 2478998 | 10/1981 | France . |
| 2499851 | 8/1982 | France . |
| 2578741 | 9/1986 | France . |
| 2617043 | 12/1988 | France . |
| 1177420 | 1/1970 | United Kingdom . |

*Primary Examiner*—Thurman K. Page
*Assistant Examiner*—Jyothsna Venkat
*Attorney, Agent, or Firm*—Oliff & Berridge

[57] ABSTRACT

Colorless or colored nail polish contains, in a polish solvent system, a film-forming substance, a resin, a plasticizer, and 0.01 to 0.5 wt. % aramide fibers (poly[paraphenylene terephthalamide]), and provides improved adhesion and strength of the polish on the nails.

9 Claims, No Drawings

5,370,866

COLORLESS OR COLORED NAIL POLISH CONTAINING ARAMIDE FIBERS

TECHNICAL FIELD

The subject of the present invention is a colored or colorless nail polish containing aramide fibers in addition to the usual ingredients.

BACKGROUND

Of the principal characteristics that nail polishes should possess, the following may be singled out in particular: good adhesion to the nail surface, and a certain flexibility and strength of the film to prevent its fragility leading to cracking of the polish.

In general, at the present time, modified resins are used to confer good adhesion and plasticizers to lead to good flexibility of the polish.

After a substantial volume of research, it has not been found that good adhesion of a colorless or colored polish to the nail surface as well as good strength can be obtained by incorporating certain fibers.

British Patent No. 1,177,420 has already proposed polishes for reinforcing and repairing broken nails, containing 0.5 to 12% of certain fibers such as for example fibers of silk, cotton, nylon, polyacrylonitrile, polyethylene terephthalate, and other polymers or copolymers.

According to this patent, the fibers present in the polish act as a nail-reinforcing agent but do not favor adhesion or strength of the polish on the nail at all.

SUMMARY OF THE INVENTION

An object of the present invention, as a novel industrial product, is a colorless or colored nail polish containing, in a polish solvent system, a film-forming substance, a resin, and a plasticizer, said polish also containing 0.01 to 0.5 wt.% of aramide fibers.

DETAILED DESCRIPTION OF PREFERRED EMBODIMENTS

The expression "aramide fibers" shall be understood to mean poly(paraphenylene terephthalamide) fibers which may be obtained by polycondensation of paraphenylenediamine and terephthalyl chloride.

Of the aramide fibers that can be used in the polishes according to the invention, the fibers known under the commercial names of "Kevlar" in particular "Kevlar Dry Pulp" sold by the duPont de Nemours Company and "Arenka" sold by the Enka Glanzstoff Company, may be cited in particular.

The length of the fibers is generally between approximately 2 and 4 mm.

According to one particular embodiment of the invention, the polish preferably contains 0.05 to 0.2 wt.% of aramide fibers.

The aramide fiber concentration is generally higher in a colorless polish than in a colored polish.

In a colorless polish or base polish, the aramide fibers confer a slightly rough appearance on the deposited film, allowing better adhesion of the colored nail polish applied subsequently without the gloss of the colored film being altered.

Moreover, application of the colored polish proves far easier as it is homogenous over the entire nail surface.

The polish solvent system according to the invention is generally present in a proportion of between 55 and 90 wt.% based on the total weight of the polish.

This solvent system may essentially be composed of a mixture of various volatile organic solvents in order to achieve relatively short drying times.

Among these solvents, acetone, ethyl acetate, butyl acetate, 2-methoxyethyl acetate, methyl ethyl ketone, methyl isobutyl ketone, methyl acetate, amyl, acetate, and isopropyl acetate can be cited.

The solvent system may also contain a diluent which is preferably a saturated linear or branched hydrocarbon such as hexane or octane or an aromatic hydrocarbon such as toluene or xylene in a proportion generally ranging from 10 to 30% relative to the total weight of the polish.

The solvent system can also contain other volatile solvents such as ethanol, n-butanol, n-propanol, isopropanol, or mixtures thereof.

The film-forming agent is generally present in the polish according to the invention in a concentration of between 5 and 20%, preferably 10 and 20 wt.%, relative to the total weight of the polish.

Of the particularly preferred film-forming agents, "RS" or "SS" type nitrocelluloses, particularly the type ¼ second RS nitrocellulose, type ½ second RS nitrocellulose, type ½ second SS nitrocellulose, and type ¾ second RS nitrocellulose should be cited.

According to the invention, ½ second nitrocellulose is preferably used.

Polyvinyl derivatives such as polyvinylbutyral as well as the copolymers described in French Patent Applications Nos. 80.07328, 81.03199 and 88.08172 may be used as the film-forming agent according to the invention.

In the polish according to the invention, the resin is generally present in a proportion of between 0.5 and 10 wt.% relative to the total weight of the polish.

Of the numerous resins that can be used, resins of the aryl-sulfonamide-formaldehyde or aryl-sulfonamide-epoxy types, particularly the toluenesulfonamide-formaldehyde resin better known under the trade name "Santolite MHP" and "Santolite MS 80%," are preferably used according to the invention, the former being harder and the latter leading to formation of a more flexible film.

These resins increase the film-forming power and improve gloss as well as adhesion.

According to the invention, the plasticizer is generally present in the polish in a concentration of between 2 and 10 wt.% relative to the total weight of the polish.

Plasticizers allow the flexibility of the film to be adjusted without weakening its resistance to physical forces. Of the plasticizers that can be used in the polishes according to the invention, the following may be cited in particular: tricresyl phosphate, benzyl benzoate, tributyl phosphate, butyl acetylricinoleate, glyceryl acetylricinoleate, dibutyl phthalate, butyl glycolate, dioctyl phthalate, butyl stearate, tributoxyethyl phosphate, triphenyl phosphate, triethyl citrate, tributyl citrate, tributyl acetylcitrate, 2-triethylhexyl acetylcitrate, dibutyl tartrate, dimethoxyethyl phthalate, diisobutyl phthalate, diamyl phthalate, camphor, glycerol triacetate, and mixtures thereof.

If one of the preferred forms of the invention is a colorless polish, this can nonetheless be colored with at least one organic or inorganic coloring agent.

Of the organic coloring agents, D & C Red Nos. 10, 11, 12 and 13, D & C Red No. 7, D & C Red Nos. 5 and 6, D and C Red No. 34, lacquers such as lacquer D & C Yellow No. 5 and lacquer D & C Red No. 2 may be cited.

Of the inorganic coloring agents, titanium dioxide, bismuth oxychloride, brown iron oxide, and red iron oxides may be cited. Guanine may also be cited as a coloring agent.

According to this embodiment, the coloring agents are generally present in a proportion of between 0.0 and 2 wt.% relative to the total weight of the polish.

The use of aramide fibers in the polishes according to the invention also has the advantage of dispensing fully or partially with substances for preventing sedimentation of coloring agents such as for example "Bentone 27" and "Bentone 38," since the aramide fibers act as thixotropic agents.

Nail polishes according to the invention can also contain the additives currently used in nail polishes. Among these additives, UV filters such as benzophenone and ethyl 2-cyano-3,3-diphenylacrylate may be cited.

Although the colorless or colored polishes according to the invention are made by classical methods, the aramide fibers should be added at the last moment before the final agitation stage.

Several examples of nail polishes according to the invention will now be provided for illustration without being limiting in nature.

|  | wt. % |
|---|---|
| EXAMPLE 1: Colorless nail polish | |
| Toluene | 21.93 |
| n-Butyl acetate | 20.03 |
| Ethyl acetate | 18.56 |
| ½ SS Nitrocellulose | 15.44 |
| Isopropyl alcohol | 8.21 |
| Tributyl acetylcitrate | 6.40 |
| Polyvinyl butyral | 2.60 |
| Hydrated silica | 2.35 |
| Toluenesulfonamide-formaldehyde resin | 1.10 |
| Bentone 27 | 1.00 |
| Ethyl 2-cyano-3,3-diphenylacrylate | 1.00 |
| Camphor | 0.90 |
| Titanium dioxide | 0.24 |
| Aramide fibers (Kevlar by duPont) | 0.15 |
| Citric acid | 0.05 |
| Benzophenone | 0.04 |
| EXAMPLE 2: Colorless nail polish | |
| Toluene | 21.30 |
| n-Butyl acetate | 19.40 |
| Ethyl acetate | 18.56 |
| ½ SS Nitrocellulose | 17.02 |
| Isopropyl alcohol | 8.21 |
| Tributyl acetylcitrate | 6.40 |
| Polyvinyl butyral | 2.60 |
| Hydrated silica | 2.35 |
| Toluenesulfonamide-epoxy resin | 1.10 |
| Bentone 27 | 1.00 |
| Ethyl 2-cyano-3,3-diphenylacrylate | 1.00 |
| Camphor | 0.90 |
| Aramide fibers (Kevlar by duPont) | 0.07 |
| Citric acid | 0.05 |

-continued

|  | wt. % |
|---|---|
| Benzophenone | 0.04 |
| EXAMPLE 3: Colored nail polish | |
| Toluene | 21.15 |
| n-Butyl acetate | 19.26 |
| Ethyl acetate | 18.43 |
| ½ SS Nitrocellulose | 16.90 |
| Isopropyl alcohol | 8.15 |
| Tributyl acetylcitrate | 6.36 |
| Polyvinyl butyral | 2.58 |
| Hydrated silica | 2.33 |
| Bentone 27 | 1.06 |
| Toluenesulfonamide-epoxy resin | 1.04 |
| Ethyl 2-cyano-3,3-diphenylacrylate | 0.99 |
| Camphor | 0.89 |
| D & C Red No. 6, barium lake | 0.36 |
| D & C Red No. 7, calcium lake | 0.21 |
| Titanium dioxide | 0.07 |
| Aramide fibers (Kevlar by duPont) | 0.07 |
| Guanine | 0.06 |
| Citric acid | 0.05 |
| Benzophenone | 0.04 |

What is claimed is:

1. A colorless or colored nail polish comprising:
   (a) 55 to 90 wt. % of a polish solvent system;
   (b) 5 to 20 wt. % of a film forming substance;
   (c) 0.5 to 10 wt. % of a resin;
   (d) 2 to 10 wt. % of a plasticizer, and
   (e) 0.01 to 0.2 wt. % of aramide fibers where in the aramide fibers are poly(paraphenylene terephthalamide) fibers.

2. Nail polish according to claim 1 wherein the aramide fibers have a length between 2 and 4 mm.

3. Nail polish according to claim 1 wherein the film-forming agent is ½ second SS nitrocellulose.

4. Nail polish according to claim 1 wherein, the resins are selected from the group consisting of aryl-sulfonamide-formaldehyde and aryl-sulfonamide-epoxy.

5. Nail polish according to claim 1, further comprising at least one coloring agent of an organic or inorganic nature.

6. Nail polish according to claim 5, wherein the coloring agent is present in a concentration of between 0.01 and 2% relative to the total weight of polish.

7. A colorless base polish conferring a slightly rough appearance by application on the nail and allowing better adhesion of a colored nail polish applied subsequently, said colorless base polish comprising:
   (a) 55 to 90 wt. % of a polish solvent system;
   (b) 5 to 20 wt. % of a film forming substance;
   (c) 0.5 to 10 wt. % of a resin;
   (d) 2 to 10 wt. % of a plasticizer, and
   (e) 0.01 to 0.2 wt. % of aramide fibers having a length between about 2 to 4 mm wherein the aramide fibers are poly(paraphenylene terephthalamide) fibers and, said aramide fibers conferring to the base polish the rough appearance on the nail.

8. The base polish of claim 7, wherein the film forming substance is ½ second SS nitrocellulose.

9. The base polish of claim 7, wherein the resin is selected from the group consisting of aryl-sulfonamide-formaldehyde and aryl-sulfonamide-epoxy.

* * * * *